(12) United States Patent
Uchida et al.

(10) Patent No.: US 6,376,106 B1
(45) Date of Patent: Apr. 23, 2002

(54) DIAMINONAPHTHALENE DERIVATIVE AND ORGANIC ELECTROLUMINESCENT DEVICE USING THE SAME

(75) Inventors: Manabu Uchida; Toshihiro Koike; Takenori Izumizawa; Kenji Furukawa, all of Kanagawa (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/212,485

(22) Filed: Dec. 16, 1998

(30) Foreign Application Priority Data

Dec. 16, 1997 (JP) .............................. 9-363500
Sep. 25, 1998 (JP) .............................. 10-271046

(51) Int. Cl.[7] ........................ H05B 33/12; C07C 211/42

(52) U.S. Cl. ...................... 428/690; 428/704; 428/917; 313/504; 313/506; 564/429

(58) Field of Search ................................ 428/690, 704, 428/917; 313/504, 506; 564/308, 309, 429; 430/58.75, 58.8

(56) References Cited

U.S. PATENT DOCUMENTS

| | | | |
|---|---|---|---|
| 4,047,948 A | 9/1977 | Horgan | |
| 4,536,457 A | 8/1985 | Tam | |
| 5,047,687 A | 9/1991 | VanSlyke | 313/503 |
| 5,312,707 A | 5/1994 | Ota et al. | 430/59 |
| 6,013,383 A | * 1/2000 | Shi et al. | 428/690 |

FOREIGN PATENT DOCUMENTS

| | | | |
|---|---|---|---|
| EP | 0 650 955 | * | 5/1995 |
| EP | 0 721 935 | | 7/1996 |
| EP | 0 797 375 | | 9/1997 |
| JP | 6-32307 | | 11/1984 |
| JP | 4-308688 | | 10/1992 |
| JP | 5-234681 | | 9/1993 |
| JP | 5-239455 | | 9/1993 |
| JP | 6-1972 | | 1/1994 |
| JP | 7-97355 | | 4/1995 |
| JP | 7-126226 | | 5/1995 |
| JP | 7-126615 | | 5/1995 |
| JP | 7-331238 | | 12/1995 |
| JP | 8-48656 | | 2/1996 |
| JP | 8-87122 | | 4/1996 |
| JP | 8-100172 | | 4/1996 |
| JP | 8-259940 | | 10/1996 |
| JP | 9-194441 | | 7/1997 |

OTHER PUBLICATIONS

J. Chem. Soc. Chem Comm 1996,2175, Novel hole–transporting materials based on triphenylamine for organic electroluminescent devices by Hiromitsu Tanaka, Shizuo Tokito, Yasunori Taga and Akane Okada. (no month).

Advanced Materials 6–677 (1994), Thermally Stable Multilayered Organic Electroluminescent Devices Using Novel Starburst Molecules by Yoshiyuki Kuwabara, Hiromitsu Ogawa, Hiroshi Inada, Naoki Noma and Yasuhiko Shirota. (no month).

J. Appl. Phys., 65,3610 Electroluminescence of doped organic thin films by . C.W. Tang, S.A. VanSlyke and C.H. Chen, May 1, 1989.

Japanese Journal of Applied Physics vol. 27, No. 2, Feb. 1998 pp. L269–L271 by Chihaya Adachi, Shizuo Tokito, Tetsuo Tsutsui and Shogo Saito, "Electroluminescence in organic Films . . . ".

Appl. Phys. Lett., 57,531 Confinement of charge carrieres and molecular excition within 5–nm thick emitter layer in organic electroluminescent devices with a double heterostructure by Chihaya Adachi, Tetsuo Tsutsui, and Shogo Saito, Aug. 6, 1990.

* cited by examiner

Primary Examiner—Marie Yamnitzky
(74) Attorney, Agent, or Firm—Sughrue Mion, PLLC

(57) ABSTRACT

A diaminonaphthalene derivative of formula (1):

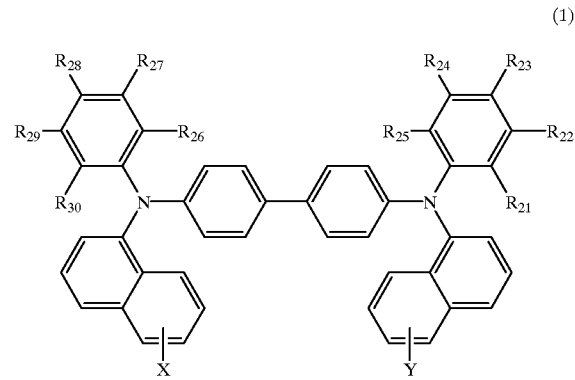

(1)

wherein $R_{21}$ to $R_{30}$ independently and individually represent a hydrogen atom, a halogen atom, a C1–C6 alkyl group, a C1–C6 alkoxy group, a substituted or unsubstituted amino group, a substituted or unsubstituted aryl group, or a substituted or unsubstituted heterocyclic group, the substituted or unsubstituted aryl group or the substituted or unsubstituted heterocyclic group may be condensed with the corresponding benzene ring at an arbitrary position of the benzene ring; and each of X and Y represents a hydrogen atom or a substituted or unsubstituted amino group, wherein at least one of the X or Y represents a substituted or unsubstituted amino group. The derivative is incorporated into an organic electroluminescent device (organic EL device), and serves as a hole-transportation layer, a luminescence layer, etc. The organic EL device containing the derivative exhibits high luminous efficacy and a prolonged service life.

8 Claims, No Drawings

DIAMINONAPHTHALENE DERIVATIVE AND ORGANIC ELECTROLUMINESCENT DEVICE USING THE SAME

BACKGROUND OF THE INVENTION

1. Field of the Invention

The present invention relates to a diaminonaphthalene derivative and to an electroluminescent material, particularly an organic electroluminescent material, using the same, as well as to an organic electroluminescent device (hereinafter abbreviated as an organic EL device).

2. Related Art

In recent years, organic EL devices have become of interest as candidates for flat displays of high brightness. In accordance with this trend, much research and development therefor has been actively performed. An organic EL device has a structure in which a luminescence layer is sandwiched by two electrodes. Holes injected from an anode and electrons injected from a cathode are united within the luminescence layer to thereby emit light. High- and low-molecular-weight materials may both be used for fabrication of organic EL devices, and both have been proven to provide organic EL devices of high brightness.

Organic EL devices are categorized into two types. One type utilizes a fluorescent-dye-added charge transportation material to form a luminescence layer (C. W. Tang, Journal of the Applied Physics, 65, 3610, 1989), and the other type employs a fluorescent dye per se to serve as the luminescence layer (see, for example, Japanese Journal of the Applied Physics, 27, L269, 1988).

Organic EL devices using a fluorescent dye per se for the luminescence layer are further grouped into the following three types. A first type is drawn to three-layered devices in which a luminescence layer is sandwiched by a hole-transportation layer and an electron-transportation layer; a second type is drawn to two-layered devices in which a hole-transportation layer and a luminescence layer are superposed one on the other; and a third type is drawn to two-layered devices in which an electron transportation layer and a luminescence layer are superposed one on the other. Thus, organic EL devices are known to have improved luminous efficacy when they have a two- or three-layered structure.

In the above-mentioned organic EL devices, the electron transportation layer contains an electron-transfer compound and has a function of transferring electrons injected from a cathode into the luminescence layer. The hole-injection layer and the hole-transportation layer both contain a hole-transfer compound and have a function of transferring holes injected from an anode into the luminescence layer. When the hole-injection layer is interposed between the anode and the luminescence layer, organic EL devices having excellent luminous performance can be realized, because an increased number of holes can be injected into the luminescence layer at a lower electric field, and in addition, electrons injected from the cathode or electron-injection layer can be confined within the luminescence layer, to thereby enhance the luminous efficacy.

However, the aforementioned conventional organic EL devices do not necessarily exhibit sufficient performance in practical application. One major reason for this may be attributed to lack of durability of the material of the devices; particularly, hole-transportation material. It has been accepted that if an irregular portion such as a grain boundary exists in the organic layer of an organic EL device, the electric field concentrates to such a portion to thereby lead to degradation and breakage of the device. Therefore, the organic layer is usually used in its amorphous state. Moreover, since an organic EL device is a current-injection-type device, if the material used has a low glass transition point, heat generated during use causes degradation of the organic EL device. From this viewpoint, materials having a high glass transition temperature (Tg) are desired.

Furthermore, hole-transportation materials used for conventional devices have insufficient hole transportability and therefore the luminous efficacy of the devices has not been satisfactory in practice.

A variety of materials centering on triphenylamine derivatives have been known as hole-transportation materials used for such organic EL devices, yet very few materials are suitable for practical use.

For example, there has been known N,N'-diphenyl-N,N'-di(3-methylphenyl)-4,4'-diaminobiphenyl (hereafter abbreviated as TPD) (Applied Physics Letter, Vol. 57, No. 6, page 531, 1990). This compound is thermally unstable, and has disadvantages in service life of the resultant device. Many other triphenylamine derivatives are disclosed in, for example, U.S. Pat. Nos. 5,047,687, 4,047,948, and 4,536,457; Japanese Patent Publication (kokoku) No. 6-32307; and Japanese Patent Application Laid-Open (kokoku) Nos. 5-234681, 5-239455, 8-87122, and 8-259940. However, none of these triphenylamine derivatives are satisfactory in terms of their characteristics.

Star-burst amine derivatives disclosed in Japanese Patent Application Laid-Open (kokai) No. 4-308688 or 6-1972, or "Advanced Material" Vol. 6, page 677 (1994) do not meet essential requirements for organic EL devices in practice, i.e., high luminous efficacy and long service life; and neither do respective compounds disclosed in Japanese Patent Application Laid-Open (kokai) Nos. 7-126226, 7-126615, 7-331238, 7-97355, 8-48656, and 8-100172, and "Journal of the Chemical Society Chemical Communication" page 2175 (1996).

Japanese Patent Application Laid-Open (kokai) No. 9-194441 discloses examples in which naphthylamine derivatives are used, and these derivatives are described as having improved characteristics as compared with TPD. However, these derivatives require improvements regarding hole transportability and heat resistance.

As described above, hole-transportation materials used in conventional organic EL devices still require improved performance, and thus there is need for an excellent material that can enhance the luminous efficacy and service life of organic EL devices.

In most cases, emission of light from organic EL devices is obtained from a luminescence layer or an electron-transportation layer which is provided independently of an electron-transportation layer; in very few cases is emission of light obtained from a hole-transportation layer. The reason for this may be partially attributed to the compatibility with the co-used electron-transportation layer; but it is also considered that the color and intensity of the luminescent light from the hole-transportation layer itself may be a critical factor. If luminescent light can be procured from a hole-transportation layer, such a technique would add value in practice. However, there are known only a few materials which serve such a purpose, and in many cases, materials which serve this purpose emit light having a long wavelength and have a disadvantage in that luminescent light having a short wavelength cannot be obtained.

SUMMARY OF THE INVENTION

In view of the foregoing, the inventors of the present invention have conducted extensive studies in an attempt to solve the aforementioned problems involved in conventional organic EL devices, and have found that when a specific type of diaminonaphthalene derivative is used, organic EL devices having a high luminous efficacy and a longer service life can be obtained, leading to completion of the present invention.

Accordingly, an object of the present invention is to provide an organic EL device having high luminous efficacy and a prolonged service life.

Another object of the present invention is to provide a novel compound which is used for the organic EL device.

A further object of the present invention is to provide a hole-transportation material which is used for the organic EL device.

A still further object of the present invention is to provide a novel organic electroluminescent material used for the device.

In a first aspect of the present invention, there is provided a diaminonaphthalene derivative of formula (1):

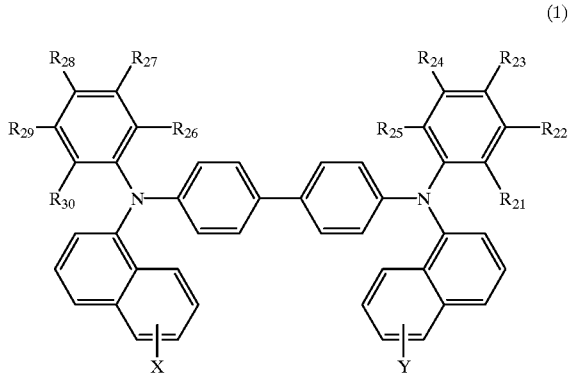

wherein $R_{21}$ to $R_{30}$ independently and individually represent a hydrogen atom, a halogen atom, a C1–C6 alkyl group, a C1–C6 alkoxy group, a substituted or unsubstituted amino group, a substituted or unsubstituted aryl group, or a substituted or unsubstituted heterocyclic group, the substituted or unsubstituted aryl group or the substituted or unsubstituted heterocyclic group may be condensed with the corresponding benzene ring at an arbitrary position of the benzene ring; and each of X and Y represents a hydrogen atom or a substituted or unsubstituted amino group, wherein at least one of the X or Y represents a substituted or unsubstituted amino group.

In the diaminonaphthalene derivative of formula (1) of the present invention, X and Y may respectively be substituted by a hydrogen atom located at any position of the naphthalene ring.

In a second aspect of the present invention, there is provided a diaminonaphthalene derivative of formula (2):

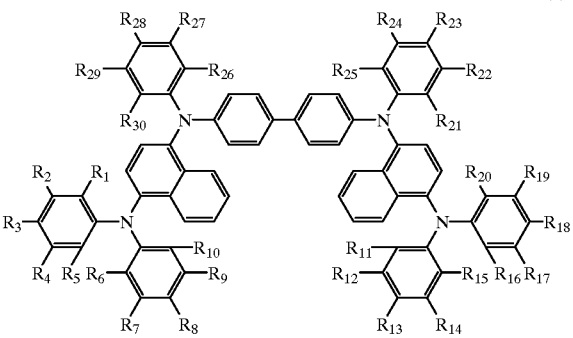

wherein $R_1$ to $R_{30}$ independently and individually represent a hydrogen atom, a halogen atom, a C1–C6 alkyl group, a C1–C6 alkoxy group, a substituted or unsubstituted amino group, a substituted or unsubstituted aryl group, or a substituted or unsubstituted heterocyclic group, the substituted or unsubstituted aryl group or the substituted or unsubstituted heterocyclic group may be condensed with the corresponding benzene ring at an arbitrary position of the benzene ring.

In a third aspect of the present invention, there is provided an organic electroluminescent device making use of the diaminonaphthalene derivative of the above-described formula (1).

In a fourth aspect of the present invention, there is provided an organic electroluminescent device comprising a hole-transportation layer, wherein the hole-transportation layer contains the diaminonaphthalene derivative of the above-described formula (1).

In a fifth aspect of the present invention, there is provided an organic electroluminescent device comprising a luminescence layer, wherein the luminescence layer contains the diaminonaphthalene derivative of the above-described formula (1).

In a sixth aspect of the present invention, there is provided an organic electroluminescent device comprising a hole-injection layer, wherein the hole-injection layer contains the diaminonaphthalene derivative of the above-described formula (1).

In a seventh aspect of the present invention, there is provided an organic electroluminescent material formed of the diaminonaphthalene derivative of the above-described formula (1).

In an eighth aspect of the present invention, there is provided a hole-transportation material formed of the diaminonaphthalene derivative of the above-described formula (1).

As described above, according to the present invention, due to the use of a specific diaminonaphthalene derivative, there can be provided organic EL devices having high luminous efficacy and a long service life, novel electroluminescent materials, hole-transportation materials, and organic electroluminescent materials.

In other words, through use of a diaminonaphthalene derivative as an organic layer, the EL devices of the present invention easily attain high luminous efficacy and prolonged service life. In addition, full-colored displays are realized with ease. Accordingly, use of an organic EL device of the present invention enables to fabricate display apparatus of high luminous efficacy, such as full-colored displays.

DESCRIPTION OF PREFERRED EMBODIMENTS
The present invention will next be described in detail.
Specific examples of the diaminonaphthalene derivatives of formula (1) include those represented by the following formulas (3) through (15):
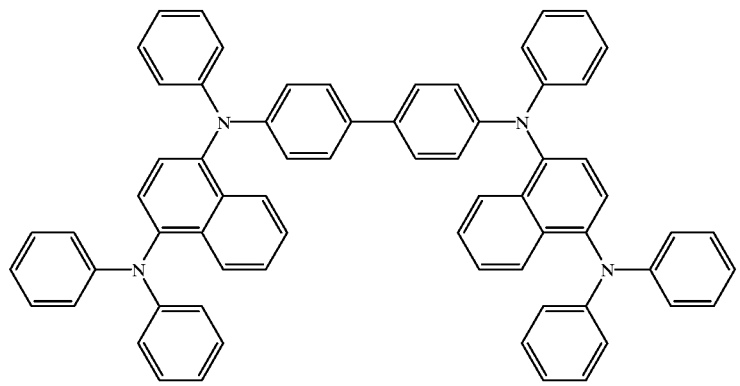
(3)
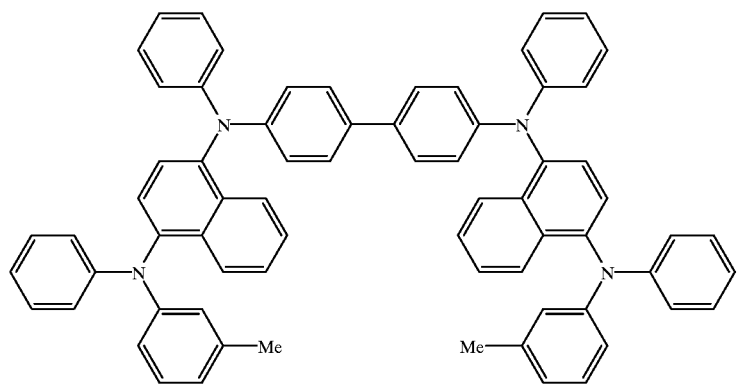
(4)
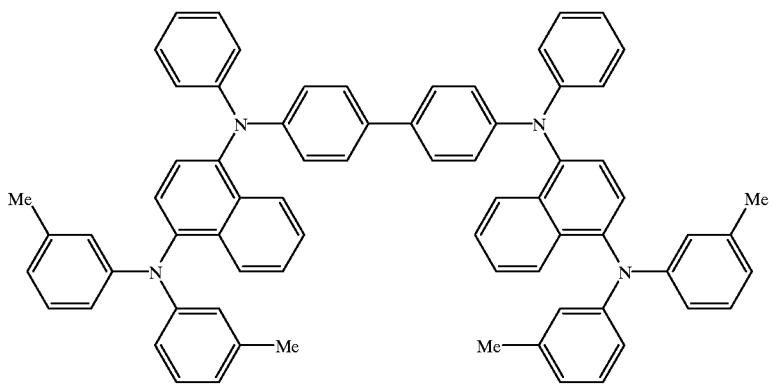
(5)

(6)
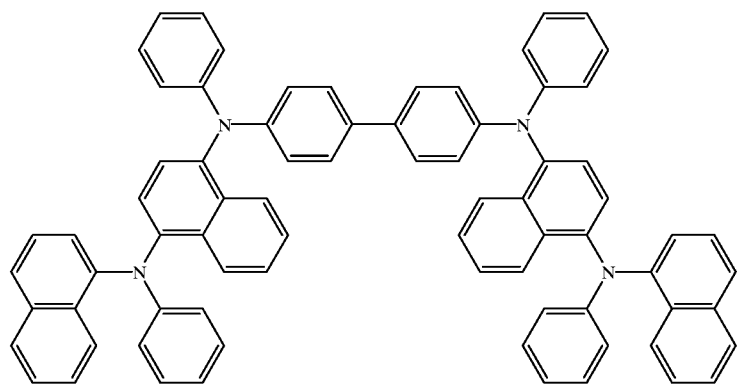
(7)
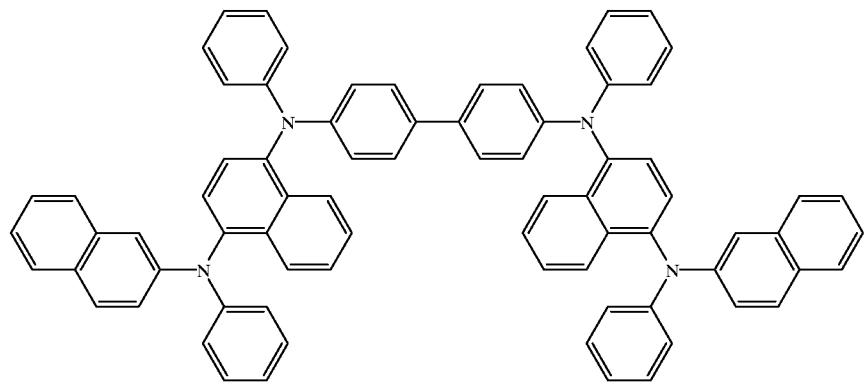
(8)
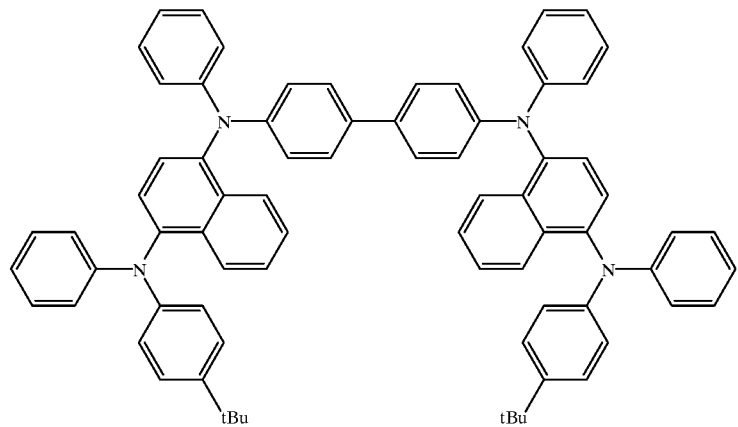
(9)
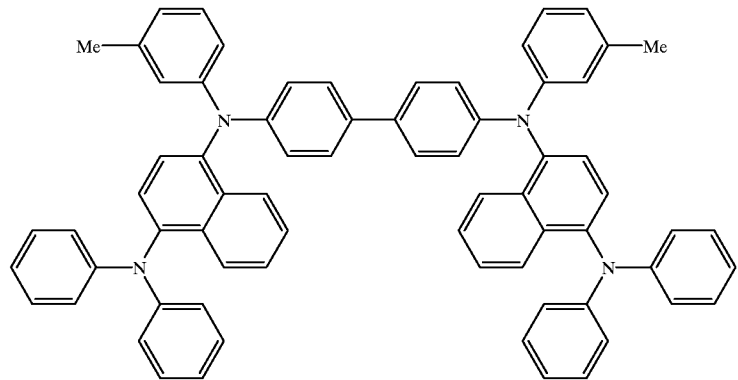

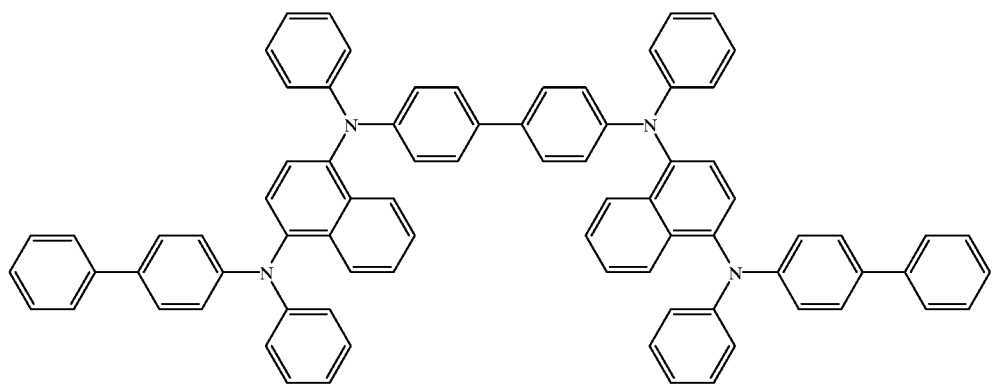
(10)
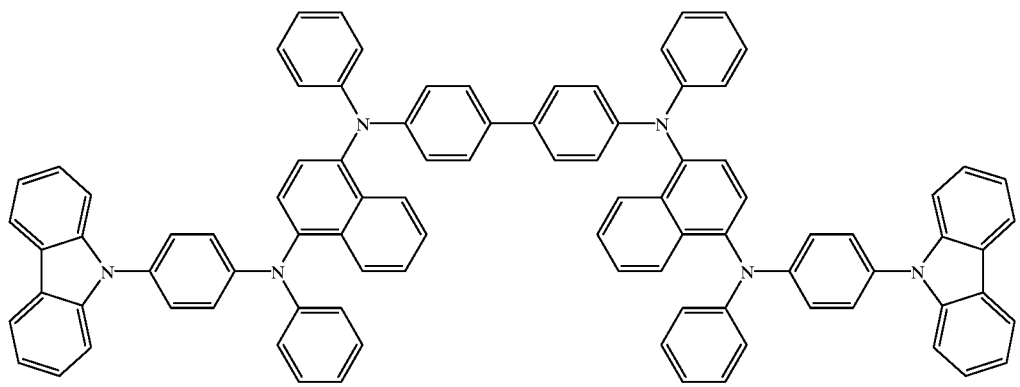
(11)
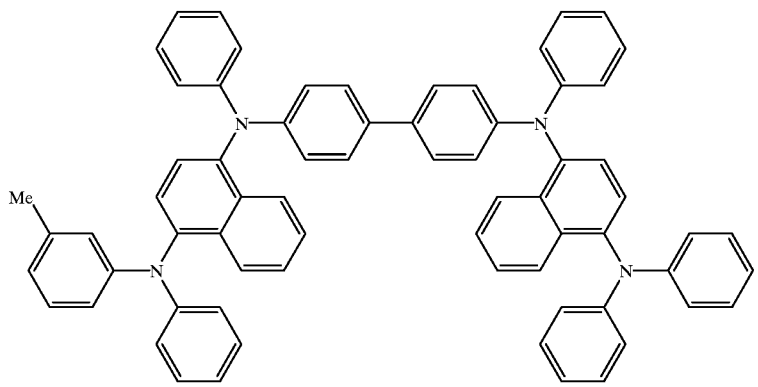
(12)
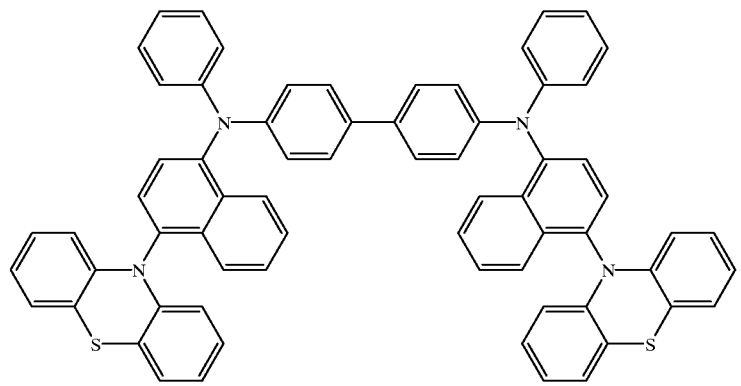
(13)

-continued

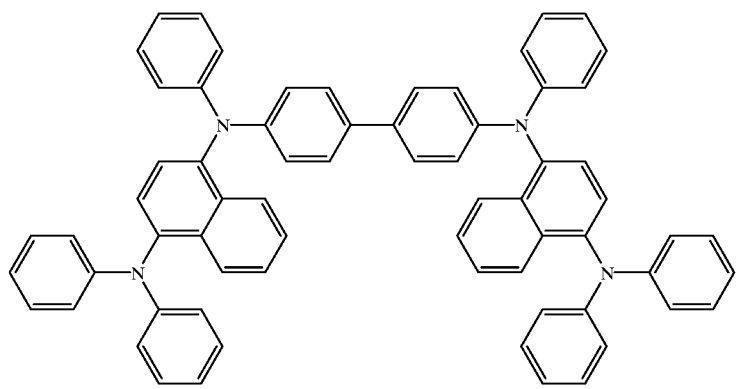

(14)

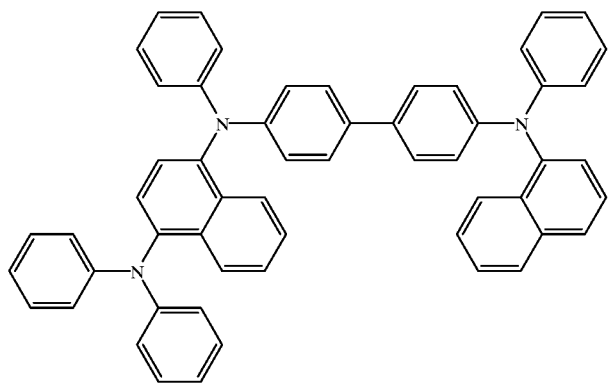

(15)

Of the compounds represented by formulas (3) through (15), those represented by formulas (3) through (13) are examples of the diaminonaphthalene derivatives of formula (2).

These diaminonaphthalene derivatives may be synthesized through a known synthesis method; for example, the methods described in Synthesis Examples of the present specification.

The diaminonaphthalene derivatives of the present invention are suitable for use as luminescent materials because of their self-fluorescence emission, which is induced by introduction of a phenylnaphthylene group. In particular, since the diaminonaphthalene derivatives of the present invention glow blue, they provide organic EL devices emitting light of different colors by incorporation of another luminescent material such as a blue, green, or red luminescent material.

In general, a compound used in an organic layer that constitutes an organic EL device preferably forms no excited complex with a compound used in another layer. The diaminonaphthalene derivatives according to the present invention have an advantage that they do not easily form an excited complex with another compound. This is considered to be due to introduction of a phenylnaphthylene group.

The organic EL devices of the present invention are endowed not only with high luminous efficacy but also with excellent durability during storage and in use. This is because the diaminonaphthalene derivatives used in the present invention have a high Tg point.

The diaminonaphthalene derivatives of formula (1) function as both a hole-transportation material and a hole-injection material.

The organic EL device of the present invention may be realized in a variety of modes. Basically, the device has a structure wherein an organic layer containing the above-described diaminonaphthalene derivative is sandwiched by a pair of electrodes (anode and cathode), and, optionally, a hole-injection material, a hole-transportation material, a luminescent material, an electron-injection material, or an electron-transportation material may be incorporated into the above-described diaminonaphthalene derivative layer. When the diaminonaphthalene derivative layer serves as a luminescence layer, another luminescent material may be incorporated thereto, to thereby emit light having a different wavelength or to obtain enhanced luminous efficacy.

Alternatively, a hole-injection material, a hole-transportation material, a luminescent material, an electron-injection material, or an electron-transportation material may be formed into a layer and laminated on the diaminonaphthalene derivative layer.

Specific structural examples include lamination structures such as (1) anode/diaminonaphthalene derivative layer/cathode; (2) anode/diaminonaphthalene derivative layer/luminescence layer/cathode; (3) anode/diaminonaphthalene derivative layer/luminescence layer/electron-injection layer/cathode; (4) anode/hole-injection layer/diaminonaphthalene derivative layer/luminescence layer/electron-injection layer/cathode; (5) anode/diaminonaphthalene derivative layer/hole-transportation layer/luminescence layer/electron-injection layer/cathode; and (6) anode/hole-injection layer/diaminonaphthalene derivative layer/electron-injection layer/cathode.

In the above cases, a hole-injection layer and an electron-injection layer are not always necessary; however, incorporation thereof enhances luminous efficacy of the EL device.

The organic EL device of the present invention, having whichever of the structures listed above, is preferably supported by a substrate. No particular limitation is imposed on the substrate, and glass, transparent plastic film, etc. may be used insofar as the material of the substrate has sufficient mechanical strength, thermal stability, and transparency.

With regard to the anode materials of the organic EL device of the present invention, there may be used a metal, an alloy, an electrically conductive compound, or a mixture thereof having a work function of more than 4 eV. Examples include metals such as Au; and conductive transparent materials such as CuI, indium tin oxide hereinafter abbreviated as ITO), $SnO_2$, or ZnO.

With regard to the cathode materials, there maybe used a metal, an alloy, an electrically conductive compound, or a mixture thereof having a work function of less than 4 eV. Examples include calcium, magnesium, lithium, aluminum, magnesium alloys, lithium alloys, aluminum alloys, and other alloys such as aluminum/lithium, magnesium/silver, or magnesium/indium.

In order to output the luminescence of an organic EL device at a high luminous efficacy, at least one electrode preferably has an optical transparency of 10% or more. The sheet resistance of the electrodes is preferably some hundreds of Ω/mm or less. The thickness of the electrodes, which depends on the electrode materials, is typically determined within the range of 10 nm–1 μm, preferably 10–400 nm. Such electrodes may be produced by forming a thin film through vapor deposition or sputtering and by use of the above-described electrode materials.

The above-described hole-injection material, hole-transportation material, luminescent material, electron injection material, or electron-transportation material may be formed into a hole-injection layer, hole-transportation layer, luminescence layer, electron injection layer, or electron-transportation layer, and these layers may be superposed on a layer containing the diaminonaphthalene derivative.

In the organic EL device of the present invention, the materials used as the hole-injection material, hole-transportation material, luminescent material, electron-injection material, etc. preferably have a Tg of 80° C. or more, more preferably 100° C. or more.

With regard to a hole-injection material and hole-transportation material, in addition to the diaminonaphthalene derivatives that are used in the organic EL device of the present invention, there may be used an arbitrary material selected from materials which have conventionally been used as charge-transportation materials for holes among photoconductive materials and from known materials which are used in a hole-injection layer or a hole-transportation layer of an organic EL device.

Examples include carbazole derivatives (e.g., N-phenylcarbazole and polyvinylcarbazole); triarylamine derivatives (e.g., TPD, polymers having an aromatic tertiary amine in a main or side chain, 1,1-bis(4-di-p-tolylaminophenyl)cyclohexane, N,N'-diphenyl-N,N'-dinaphthyl-4,4'-diaminobiphenyl, 4,4',4"-tris{N-(3-methylphenyl)-N-phenylamino}triphenylamine, compounds described in "Journal of the Chemical Society Chemical Communication" page 2175 (1996), compounds described in Japanese Patent Application Laid-Open (kokai) Nos. 57-144558, 61-62038, 61-124949, 61-134354, 61-134355, 61-112164, 4-308688, 6-312979, 6-267658, 7-90256, 7-97355, 6-1972, 7-126226, 7-126615, 7-331238, 8-100172, and 8-48656, and star-burst amine derivatives described in "Advanced Materials" Vol. 6, page 677 (1994)); stilbene derivatives (e.g., a compound described in Proceedings (II) of the 72th annual spring convention of The Chemical Society of Japan); phthalocyanine derivatives (e.g., metal-free phthalocyanine, copper phthalocyanine); and polysilane.

Each of a hole-injection layer and a hole-transportation layer of the organic EL device of the present invention may be formed of a single layer containing one or more species of the above-described compounds, or may comprise a plurality of layers laminated one on another, wherein the layers contain different species of compounds.

No particular limitation is imposed on the electron-injection material and the electron-transportation material that are used in the organic EL device of the present invention, and there may be used an arbitrary material selected from materials which have conventionally been used as electron-transportation materials among photoconductive materials and from known materials which are used in an electron-injection layer and an electron-transportation layer of organic EL devices.

Examples of such electron-transfer compounds include diphenylquinone derivatives (e.g., described in *Denshi-Shashin Gakkai-shi,* 30, 3 (1991)); perylene derivatives (e.g., described in J. Apply. Phys., 27, 296 (1988)); oxadiazole derivatives (e.g., described in the above-described literature, Jpn. J. Appl. Phys., 27, L713 (1988), or Appl. Phys. Lett., 55, 1489 (1989)); thiophene derivatives (e.g., described in Japanese Patent Application (kokai) No. 4-212286); triazole derivatives (e.g., described in Jpn. J. Appl. Phys., 32, L917 (1993)); thiadiazole derivatives (e.g., described in the 43th Proceedings of The Society of Polymer Science, Japan, (III) Pla007)); metal complexes of an oxine derivative (the technical research report of *Denshi Jyoho Tsushin Gakkai,* 92(311), 43 (1992)); polymers of a quinoxaline derivative (e.g., described in Jpn. J. Appl. Phys., 33, L250 (1994)); and phenanthroline derivatives (e.g., described in the 43th Proceedings of *Kobunshi Toronkai,* 14J07).

With regard to other luminescent material used in the organic EL device of the present invention other than the diaminonaphthalene derivative, there may be used known luminescent materials, such as daylight fluorescent materials, fluorescent brighteners, laser dyes, organic scintillators, and reagents for fluorescent analysis, as described in "Hikari Kinou Zairyo" in *Kobunshi Kinou Zairyo* series, published by Kyoritsu Shuppan (1991), P236, edited by The Society of Polymer Science, Japan.

Specifically, preferable examples of the luminescent material include polycondensed ring compounds such as anthracene, phenanthrene, pyrene, chrysene, perylene, coronene, rubrene, and quinacridone; oligophenylene compounds such as quaterphenyl; scintillators for liquid scintillation such as 1,4-bis(2-methylstyryl)benzene, 1,4-bis(4-methylstyryl)benzene, 1,4-bis(4-methyl-5-phenyl-2-oxazolyl)benzene, 1,4-bis(5-phenyl-2-oxazolyl)benzene, 2,5-bis(5-tert-butyl-2-benzoxazolyl)thiophene, 1,4-diphenyl-1,3-butadiene, 1,6-diphenyl-1,3,5-hexatriene, or 1,1,4,4-tetraphenyl-1,3-butadiene, a metal complex of an oxine derivative described in Japanese Patent Application (kokai) No. 63-264692; coumarin dyes; dicyanomethylenepyran dyes; dicyanomethylenethiopyran dyes; polymethine dyes; oxobenzanthracene dyes; xanthene dyes; carbostyryl dyes; perylene dyes; an oxazine compound described in German Patent No. 2534713; a stilbene derivative described in the Proceedings of the 40th Joint Lecture of Applied Physics, 1146 (1993); a spiro compound described in Japanese Patent Application (kokai) No. 7-278537; and an oxadiazole compound described in Japanese Patent Application (kokai) No. 4-393891.

Respective layers which constitute the organic EL device of the present invention may be produced by forming a thin film through a known method such as vapor-deposition, spin-coating or casting and by use of materials for respective layers.

No particular limitation is imposed on the film thickness of the thus-obtained respective layers, and it may be selected in accordance with characteristics of the material. It is typically determined within the range of 2 nm–5000 nm.

In order to form thin film of a diaminonaphthalene derivative, a vapor deposition method is preferably employed, in consideration that homogeneous film is easily produced and pinholes are difficult to generate. When thin film formation is preformed through a vapor deposition method, the desirable vapor deposition conditions are typically determined within the following ranges: boat heating temperature of 50–400° C., degree of vacuum of $10^{-6}$–$10^{-3}$ Pa, vapor deposition rate of 0.01–50 nm/sec, substrate temperature from −150 to +300° C., and film thickness of 5 nm–5 μm, in accordance with species of diaminonaphthalene derivatives and crystal structure and association structure of target molecular accumulated films.

A method for producing an organic EL device using the diaminonaphthalene derivative of the present invention will next be described with reference to the case of an organic EL device formed of the above-described anode/ diaminonaphthalene layer/cathode as an example. The target organic EL device is obtained through a method comprising the steps of fabricating an anode by forming a thin film comprising an anode material having a thickness of 1 μm or less, preferably 10–200 nm, on an appropriate substrate through vapor deposition; coating the anode with a thin film of diaminonaphthalene derivative, to thereby produce a luminescence layer; and coating the luminescence layer with a thin film comprising a cathode material so as to attain a film thickness of 1 μm or less, to thereby produce a cathode.

Alternatively, the above-described method may be performed in a reverse manner, i.e., successively forming a cathode, a luminescent layer, and an anode, in this sequence.

DC voltage is applied to the thus-obtained organic EL device, with polarity of the anode being positive (+) and the cathode negative (−). When the application voltage is 2–40 V, luminescence is observed through a transparent or opaque electrode (either anode or cathode, or both electrodes).

The organic EL device also generates luminescence when an AC voltage is applied thereto. In this case, the applied AC may have an arbitrary waveform.

EXAMPLES

The present invention will next be described by way of example. Method for Measuring Glass Transition Point Glass transition point (Tg) was measured by the following method. Briefly, a melted sample was quenched to vitrify. Subsequently, the sample's temperature was elevated at a rate of 40° C./minute, and Tg was measured by a differential scanning calorimeter (DSC).

Synthesis Example 1

Synthesis of N,N'-bis(4-diphenylamino-1-naphthyl)-N, N'-diphenyl-4,4'-benzidine (hereafter abbreviated as "DPBNDAB"; a compound of formula (3)):

N,N-diphenyl-(4-bromo-1-naphthyl)amine (1.91 g), diphenylbenzidine (0.86 g), 18-crown-6 (0.07 g), copper (0.48 g), potassium carbonate (1.41 g), and quinoline (8 ml) were charged in a flask and the contents were heated at 200° C. for 94 hours under nitrogen. After the flask was allowed to cool, the solid matter was removed by filtration, and quinoline was distilled off under reduced pressure. The residue was purified by silica gel column chromatography (heptane/ethyl acetate=3/1), to thereby obtain the target compound (0.4 g). The fluorescent color of the compound in toluene was bluish purple, and Tg of the compound was 157° C.

$^1$H-NMR(CDCl$_3$) δ=6.9–7.0 (m, 6H), 7.0–7.1 (m, 16H), 7.2–7.3 (m, 12H), 7.3–7.4 (m, 8H), 7.41 (d, 4H), 8.0 (m, 4H).

Synthesis Example 2

Synthesis of N,N'-bis{4-N"-(3-methylphenyl)-N"-phenylamino-1-naphthyl}-N,N'-diphenyl-4,4'-benzidine (a compound of formula (6)):

The procedure of Synthesis Example 1 was repeated except that N-phenyl-N-(3-methylphenyl)-(4-bromo-1-naphthyl)amine was used instead of N,N-diphenyl-(4-bromo-1-naphthyl)amine.

Synthesis Example 3

Synthesis of N,N'-bis(4-diphenylamino-1-naphthyl)-N, N'-bis(3-methylphenyl)-4,4'-benzidine (a compound of formula (9)):

The procedure of Synthesis Example 1 was repeated except that N,N'-bis(3-methylphenyl)benzidine was used instead of diphenylbenzidine.

Synthesis Example 4

Synthesis of N, N'-bis(5-diphenylamino-1-naphthyl)-N, N'-diphenyl-4,4'-benzidine (a compound of formula (14)):

The procedure of Synthesis Example 1 was repeated except that N,N-diphenyl-(5-bromo-1-naphthyl)amine was used instead of N,N-diphenyl-(4-bromo-1-naphthyl)amine.

$^1$H-NMR(CDCl$_3$) δ=6.9–7.0 (m, 6H), 7.0–7.1 (m, 16H), 7.2–7.4 (m, 20H), 7.41 (m, 4H), 7.91 (m, 4H).

Synthesis Example 5

Synthesis of N-(1-naphthyl)-N'-{4-diphenylamino-1-naphthyl}-N,N'-diphenyl-4,4'-benzidine (a compound of formula (15)):

The procedure of Synthesis Example 1 was repeated except that N,N'-diphenyl-N-(1-naphthyl)benzidine was used instead of diphenylbenzidine. Tg of the compound was 135° C.

$^1$H-NMR(CDCl$_3$) δ=6.9–7.0 (m, 4H), 7.0–7.1 (m, 12H), 7.1–7.3 (m, 8H), 7.3–7.5 (m, 12H), 7.78 (d, 1H), 7.89 (d, 1H), 7.97 (d, 1H), 8.0 (m, 2H).

Example 1

ITO was vapor-deposited to a thickness of 50 nm on a glass substrate (25 mm×75 mm×1.1 mm) (produced by Tokyo San'yoshinku K.K.), and the resultant glass was used as a transparent support substrate. The support substrate was fixed upon a substrate holder of a commercially available deposition apparatus (produced by Shinkukiko K.K.). A quartz crucible containing DPBNDAB synthesized in Synthesis Example 1, a quartz crucible containing 1-allyl-1,2, 3,4,5-pentaphenylsilacyclopentadiene (APS), a graphite crucible containing magnesium, and a graphite crucible containing silver were mounted on the apparatus.

The internal pressure of the vacuum vessel was reduced to $1×10^{-3}$ Pa. The crucible containing DPBNDAB was heated for vapor deposition to form a hole-transportation layer on the support substrate, so as to attain a DPBNDAB film thickness of 50 nm. Then, the crucible containing APS was heated for vapor deposition of APS thereon to form a luminescence layer having a DPBNDAB film thickness of 50 nm. The vapor deposition rates were 0.1–0.2 nm/sec.

Subsequently, the internal pressure of the vacuum vessel was reduced to $2 \times 10^{-4}$ Pa. The graphite crucible containing magnesium was heated for vapor deposition of magnesium at a deposition rate of 1.2–2.4 nm/sec, and simultaneously, silver was vapor-deposited at a rate of 0.1–0.2 nm/sec. Thereafter, an Mg—Ag alloy electrode (200 nm) was formed on the thus-formed organic layer, to thereby obtain an organic EL device.

When a DC voltage of 6.5 V was applied between the ITO electrode serving as a positive electrode and the Mg—Ag alloy electrode serving as a negative electrode, a current of about 20 mA/cm$^2$ flowed and green light having a luminance of about 200 cd/m$^2$ and a wavelength of 503 nm emitted.

When a DC voltage of 6.5 V was continually applied at 80° C., emission of light continued even after one hour.

Example 2

The procedure of Example 1 was repeated except that tris(8-hydroxyquinoline)aluminum (ALQ) was used instead of APS, to thereby obtain an organic EL device.

When a DC voltage of 5 V was applied between the ITO electrode serving as a positive electrode and the Mg—Ag alloy electrode serving as a negative electrode, a current of about 8 mA/cm$^2$ flowed and green light emitted.

Example 3

In a manner similar to that described in Example 1, a transparent support substrate was fixed upon a substrate holder of a deposition apparatus. A quartz crucible containing DPBNDAB synthesized in Synthesis Example 1, a quartz crucible containing TPD, a quartz crucible containing ALQ, a graphite crucible containing magnesium, and a graphite crucible containing silver were mounted on the apparatus.

The internal pressure of the vacuum vessel was reduced to $1 \times 10^{-3}$ Pa. The crucible containing DPBNDAB was heated for vapor deposition to form a hole-injection layer on the support substrate, so as to attain a DPBNDAB film thickness of 10 nm. Then, the crucible containing TPD was heated for vapor deposition of TPD thereon to form a hole-transportation later having a thickness of 40 nm. Thereafter, the crucible containing ALQ was heated for vapor deposition of ALQ thereon to form a luminescence layer having a thickness of 50 nm. The vapor deposition rates were 0.1–0.2 nm/sec.

Subsequently, the internal pressure of the vacuum vessel was reduced to $2 \times 10^{-4}$ Pa. The graphite crucible containing magnesium was heated for vapor deposition of magnesium at a deposition rate of 1.2–2.4 nm/sec, and simultaneously, silver was vapor-deposited at a rate of 0.1–0.2 nm/sec. Thereafter, an Mg—Ag alloy electrode (200 nm) was formed on the thus-formed organic layer, to thereby obtain an organic EL device.

When a DC voltage of 5 V was applied between the ITO electrode serving as a positive electrode and the Mg—Ag alloy electrode serving as a negative electrode, a current of about 5 mA/cm$^2$ flowed and green light having a luminance of about 150 cd/m$^2$ emitted.

Example 4

In a manner similar to that described in Example 1, a transparent support substrate was fixed upon a substrate holder of a deposition apparatus. A quartz crucible containing DPBNDAB synthesized in Synthesis Example 1, a quartz crucible containing TPD, a quartz crucible containing 9,9'-spirobisilafluorene, a graphite crucible containing magnesium, and a graphite crucible containing silver were mounted on the apparatus.

The internal pressure of the vacuum vessel was reduced to $1 \times 10^{-3}$ Pa. The crucible containing TPD was heated for vapor deposition to form a hole-transportation layer on the support substrate, so as to attain a TPD film thickness of 5 nm. Then, the crucible containing DPBNDAB was heated for vapor deposition of DPBNDAB thereon to form a luminescence layer having a thickness of 20 nm. Thereafter, the crucible containing 9,9'-spirobisilafluorene was heated for vapor deposition of 9,9'-spirobisilafluorene thereon to form an electron-transportation layer having a thickness of 50 nm. The vapor deposition rates were 0.1–0.2 nm/sec.

Subsequently, the internal pressure of the vacuum vessel was reduced to $2 \times 10^{-4}$ Pa. The graphite crucible containing magnesium was heated for vapor deposition of magnesium at a deposition rate of 1.2–2.4 nm/sec, and simultaneously, silver was vapor-deposited at a rate of 0.1–0.2 nm/sec. Thereafter, an Mg—Ag alloy electrode (200 nm) was formed on the thus-formed organic layer, to thereby obtain an organic EL device.

When a DC voltage of 5 V was applied between the ITO electrode serving as a positive electrode and the Mg—Ag alloy electrode serving as a negative electrode, a current of about 5 mA/cm$^2$ flowed and blue light emitted from the DPBNDAB.

Example 5

In a manner similar to that described in Example 1, a transparent support substrate was fixed upon a substrate holder of a deposition apparatus. A quartz crucible containing DPBNDAB synthesized in Synthesis Example 1, a quartz crucible containing 4,4',4"-tris{N-(3-methylphenyl)-N-phenylamino}triphenylamine, a quartz crucible containing 2,5-bis{5-(2-benzo[b]thienyl)thienyl}-1,1,3,4-tetraphenylsilacyclopentadiene, a graphite crucible containing magnesium, and a graphite crucible containing silver were mounted on the apparatus.

The internal pressure of the vacuum vessel was reduced to $1 \times 10^{-3}$ Pa. The crucible containing 4,4',4"-tris{N-(3-methylphenyl)-N-phenylamino}triphenylamine was heated for vapor deposition of 4,4',4"-tris{N-(3-methylphenyl)-N-phenylamino}triphenylamine to form a hole-transportation layer of 4,4',4"-tris{N-(3-methylphenyl)-N-phenylamino}triphenylamine on the support substrate. Then, the crucible containing DPBNDAB was heated for vapor deposition of DPBNDAB thereon to form a luminescence layer having a thickness of 20 nm. Thereafter, the crucible containing 2,5-bis{5-(2-benzo[b]thienyl)thienyl}-1,1,3,4 -tetraphenylsilacyclopentadiene was heated for vapor deposition of 2,5-bis{5-(2-benzo[b]thienyl)thienyl}-1,1,3,4-tetraphenylsilacyclopentadiene thereon to form an electron-transportation layer having a thickness of 50 nm. The vapor deposition rates were 0.1–0.2 nm/sec.

Subsequently, the internal pressure of the vacuum vessel was reduced to $2 \times 10^{-4}$ Pa. The graphite crucible containing magnesium was heated for vapor deposition of magnesium at a deposition rate of 1.2–2.4 nm/sec, and simultaneously, silver was vapor-deposited at a rate of 0.1–0.2 nm/sec. Thereafter, an Mg—Ag alloy electrode (200 nm) was formed on the thus-formed organic layer, to thereby obtain an organic EL device.

When a DC voltage of 10 V was applied between the ITO electrode serving as a positive electrode and the Mg—Ag alloy electrode serving as a negative electrode, a current of about 100 mA/cm² flowed and red light emitted.

Example 6

The procedure of Example 1 was repeated except that bis[N,N'-{4-N"-(3-methylphenyl)-N"-phenylamino-1-naphthyl}-N,N'-diphenyl]-4,4'-benzidine synthesized in Synthesis Example 2 was used instead of DPBNDAB, to thereby obtain an organic EL device.

When a DC voltage of 6 V was applied between the ITO electrode serving as a positive electrode and the Mg—Ag alloy electrode serving as a negative electrode, a current of about 15 mA/cm² flowed and green light was obtained.

Example 7

The procedure of Example 1 was repeated except that bis{N,N'-(4-diphenylamino-1-naphthyl}-N,N'-bis(3-methylphenyl)}-4,4'-benzidine was used instead of DPBNADB, to thereby obtain an organic EL device.

When a DC voltage of 6.5 V was applied between the ITO electrode serving as a positive electrode and the Mg—Ag alloy electrode serving as a negative electrode, a current of about 22 mA/cm² flowed and green light emitted.

Example 8

The procedure of Example 2 was repeated except that bis[N,N'-{5-N",N"-diphenylamino-1-naphthyl}-N,N'-diphenyl]-4,4'-benzidine was used instead of DPBNDAB, to thereby obtain an organic EL device.

When a DC voltage of 5.5 V was applied between the ITO electrode serving as a positive electrode and the Mg—Ag alloy electrode serving as a negative electrode, a current of about 8 mA/cm² flowed and green light was obtained.

Example 9

The procedure of Example 2 was repeated except that [N-(1-naphthyl)-N'-{4-N,N"-diphenylamino-1-naphthyl}-N,N'-diphenyl]-4,4'-benzidine was used instead of DPBNDAB, to thereby obtain an organic EL device.

When a DC voltage of 3.9 V was applied between the ITO electrode serving as a positive electrode and the Mg—Ag alloy electrode serving as a negative electrode, a current of about 5 mA/cm² flowed and green light was obtained.

Comparative Example 1

The procedure of Example 1 was repeated except that TPD was used instead of DPBNDAB, to thereby obtain an organic EL device.

When a DC voltage of 7.5 V was applied between the ITO electrode serving as a positive electrode and the Mg—Ag alloy electrode serving as a negative electrode, a current of about 20 mA/cm² flowed and green light of 200 cd/m² emitted. The wavelength of the light was 503 nm.

However, emission of light ended after several seconds of application of a DC voltage at 80° C.

What is claimed is:

1. A diaminonaphthalene derivative of formula (1):

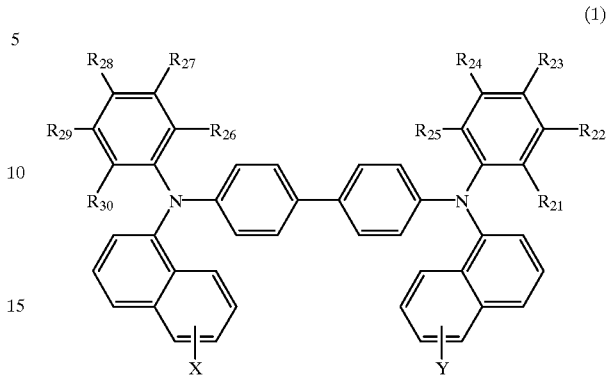

(1)

wherein $R_{21}$ to $R_{30}$ independently and individually represent a hydrogen atom, a halogen atom, a C1–C6 alkyl group, a C1–C6 alkoxy group, a substituted or unsubstituted amino group, a substituted or unsubstituted aryl group, or a substituted or unsubstituted heterocyclic group, the substituted or unsubstituted aryl group or the substituted or unsubstituted heterocyclic group may be condensed with the corresponding benzene ring at an arbitrary position of the benzene ring; and both of X and Y represent a substituted amino group, the diaminonaphthalene derivative having a glass transition temperature higher than 100° C.

2. A diaminonaphthalene derivative of formula (2):

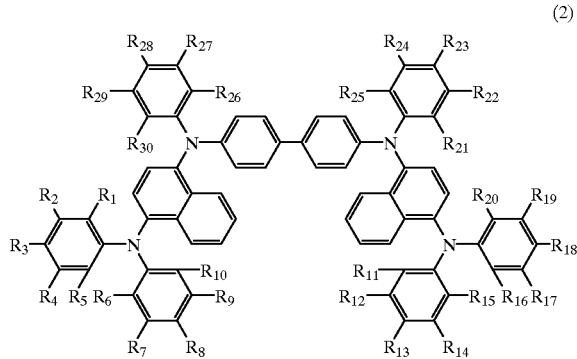

(2)

wherein $R_1$ to $R_{30}$ independently and individually represent a hydrogen atom, a halogen atom, a C1–C6 alkyl group, a C1–C6 alkoxy group, a substituted or unsubstituted amino group, an unsubstituted aryl group, or a substituted or unsubstituted heterocyclic group, the unsubstituted aryl group or the substituted or unsubstituted heterocyclic group may be condensed with the corresponding benzene ring at an arbitrary position of the benzene ring, the diaminonaphthalene derivative having a glass transition temperature higher than 100° C.

3. An organic electroluminescent device comprising at least an organic layer interposed between a pair of electrodes, wherein the organic layer contains the diaminonaphthalene derivative as described in claim 1.

4. An organic electroluminescent device comprising at least a hole-transportation layer interposed between a pair of electrodes, wherein the hole-transportation layer contains the diaminonaphthalene derivative as described in claim 1.

5. An organic electroluminescent device comprising at least a luminescence layer interposed between a pair of electrodes, wherein the luminescence layer contains the diaminonaphthalene derivative as described in claim 1.

6. An organic electroluminescent device comprising at least a hole-injection layer interposed between a pair of electrodes, wherein the hole-injection layer contains the diaminonaphthalene derivative as described in claim 1.

7. An organic electroluminescent material comprising the diaminonaphthalene derivative as described in claim 1.

8. A hole-transportation material comprising the diaminonaphthalene derivative as described in claim 1.

* * * * *